(12) United States Patent
Gehre et al.

(10) Patent No.: US 12,718,944 B2
(45) Date of Patent: Aug. 25, 2026

(54) ASSISTANCE IN THE DETECTION OF PULMONARY DISEASES

(71) Applicant: BAYER AKTIENGESELLSCHAFT, Leverkusen (DE)

(72) Inventors: Anne Claudia Gehre, Grevenbroich (DE); Bjorn Labitzke, Cologne (DE); Abdullah Shafin, Leverkusen (DE); Holger Diedam, Cologne (DE)

(73) Assignee: BAYER AKTIENGESELLSCHAFT, Leverkusen (DE)

( * ) Notice: Subject to any disclaimer, the term of this patent is extended or adjusted under 35 U.S.C. 154(b) by 1064 days.

(21) Appl. No.: 17/756,484

(22) PCT Filed: Nov. 23, 2020

(86) PCT No.: PCT/EP2020/083003

§ 371 (c)(1),
(2) Date: May 26, 2022

(87) PCT Pub. No.: WO2021/110446

PCT Pub. Date: Jun. 10, 2021

(65) Prior Publication Data

US 2023/0029547 A1 Feb. 2, 2023

(30) Foreign Application Priority Data

Dec. 5, 2019 (EP) .................................... 19213939
Jan. 10, 2020 (EP) .................................... 20151108

(51) Int. Cl.
*G16H 50/20* (2018.01)
*G16H 30/40* (2018.01)

(52) U.S. Cl.
CPC ............ *G16H 50/20* (2018.01); *G16H 30/40* (2018.01)

(58) Field of Classification Search
None
See application file for complete search history.

(56) References Cited

U.S. PATENT DOCUMENTS

| | | | |
|---|---|---|---|
| 732,697 | A | 7/1903 | Bates |
| 5,732,697 | A | 3/1998 | Zhang et al. |
| 5,840,026 | A | 11/1998 | Uber, III et al. |
| 6,039,931 | A | 3/2000 | Schmitt-Willich et al. |
| 6,643,537 | B1 | 11/2003 | Zatezalo et al. |

(Continued)

FOREIGN PATENT DOCUMENTS

| | | | |
|---|---|---|---|
| CN | 104769641 | A | 7/2015 |
| CN | 107492090 | A | 12/2017 |

(Continued)

OTHER PUBLICATIONS

Choi Jun-Ho et al. "EmbraceNet: a robust deep learning architecture for multimodal classification", pp. 259-270 [Submitted by Applicant with corresponding IDS dated Jul. 12, 2022] (Year: 2019).*

(Continued)

*Primary Examiner* — Miya J Cato

(57) ABSTRACT

The present disclosure relates to the detection of acute respiratory distress syndrome in a patient. Subjects of the present disclosure are a computer system, a method and a computer program product for detection of acute respiratory distress syndrome.

11 Claims, 6 Drawing Sheets

(56) References Cited

Figure 1:
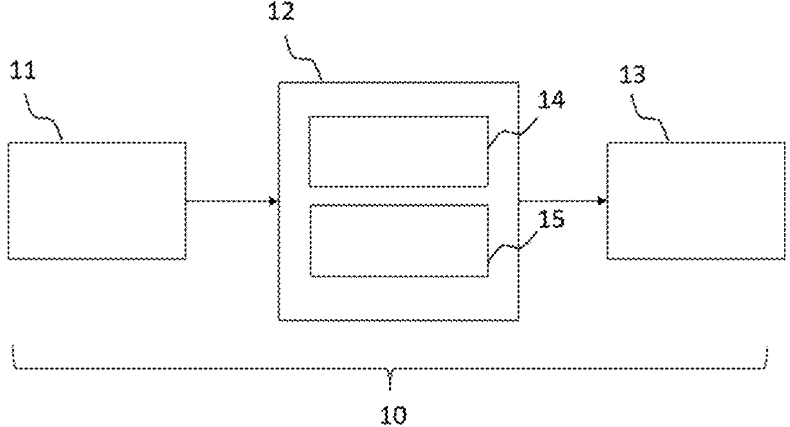

U.S. PATENT DOCUMENTS 6,754,376 B1 6/2004 Turek et al.
6,819,790 B2 11/2004 Suzuki et al.
7,564,990 B2 7/2009 Kern et al.
7,738,683 B2 6/2010 Cahill et al.
7,853,309 B2 12/2010 Ichihara et al.
7,937,134 B2 5/2011 Uber et al.
7,949,167 B2 5/2011 Krishnan et al.
8,060,178 B2 11/2011 Zhou et al.
8,155,406 B2 4/2012 Mattiuzzi
9,311,702 B2 4/2016 Pautot
9,449,381 B2 9/2016 Liang
9,616,166 B2 4/2017 Kalafut et al.
9,754,371 B2 9/2017 Kateb et al.
9,959,615 B2 5/2018 Liang et al.
10,157,467 B2 12/2018 Dincer et al.
10,176,408 B2 1/2019 Paik et al.
10,335,106 B2 7/2019 Kim
10,555,773 B2 2/2020 Higaki et al.
10,634,753 B2 4/2020 De Weerdt
10,645,359 B2 5/2020 Bist et al.
10,933,186 B2 3/2021 Uber, III
11,246,558 B2 2/2022 Uber, III et al.
11,308,613 B2 4/2022 Chitiboi et al.
2005/0100208 A1 5/2005 Suzuki et al.
2006/0018524 A1 1/2006 Suzuki et al.
2007/0047787 A1 3/2007 Oakley et al.
2008/0247622 A1 10/2008 Aylward et al.
2008/0317315 A1 12/2008 Stemmer
2009/0143669 A1 6/2009 Harms et al.
2010/0198054 A1 8/2010 Ewing et al.
2011/0029248 A1* 2/2011 Saeed ............... A61M 16/0051 702/19
2013/0035921 A1 2/2013 Rodriguez-Ponce et al.
2013/0297554 A1 11/2013 Mah
2014/0062481 A1 3/2014 Greiser et al.
2014/0257854 A1 9/2014 Becker et al.
2015/0125398 A1 5/2015 Assouline et al.
2016/0000945 A1 1/2016 Nedergaard et al.
2016/0035093 A1 2/2016 Kateb et al.
2016/0038092 A1 2/2016 Golay
2016/0109539 A1 4/2016 Mardor et al.
2017/0065241 A1 3/2017 Hoernig
2017/0243349 A1 8/2017 Hou et al.
2017/0245817 A1 8/2017 Berlin et al.
2017/0269182 A1 9/2017 Beck
2017/0281278 A1 10/2017 Higaki et al.
2018/0242917 A1 8/2018 Bagherzadeh et al.
2018/0303960 A1 10/2018 Meijer et al.
2018/0315183 A1 11/2018 Milioni De Carvalho et al.
2018/0374246 A1 12/2018 Igarashi et al.
2019/0012932 A1 1/2019 Higaki et al.
2019/0099145 A1 4/2019 Kim
2019/0122348 A1 4/2019 Jensen
2019/0205733 A1* 7/2019 Ghaeini ................. G16H 50/20
2019/0310338 A1 10/2019 James et al.
2019/0317171 A1 10/2019 Nayak et al.
2019/0318474 A1 10/2019 Han
2019/0362522 A1 11/2019 Han
2019/0365340 A1 12/2019 Hao et al.
2020/0134876 A1 4/2020 Park et al.
2020/0167911 A1 5/2020 Park et al.
2020/0202557 A1 6/2020 Schmidt
2020/0242744 A1 7/2020 Schafer et al.
2020/0258629 A1 8/2020 Ahmad et al.
2020/0311932 A1 10/2020 Hooper et al.
2020/0333414 A1 10/2020 Hilbert et al.
2020/0371182 A1 11/2020 Grimm et al.
2021/0012486 A1 1/2021 Huang et al.
2021/0027436 A1 1/2021 Banerjee et al.
2021/0027502 A1 1/2021 Abumoussa et al.
2021/0056734 A1 2/2021 Han
2021/0386389 A1 12/2021 Freiman et al.
2022/0018924 A1 1/2022 Bai et al.
2022/0031270 A1 2/2022 Cohen et al.
2022/0105265 A1 4/2022 Cowan et al.
2022/0198734 A1 6/2022 Kudo et al.
2022/0351369 A1 11/2022 Haase et al.
2022/0409145 A1 12/2022 Knobloch

FOREIGN PATENT DOCUMENTS

CN 108324244 A 7/2018
CN 109983474 A 7/2019
EP 1941460 A1 7/2008
EP 2626718 A1 8/2013
EP 2750102 A1 7/2014
EP 3118644 A1 1/2017
EP 3322997 A1 5/2018
EP 1941460 B1 12/2018
EP 3619631 A1 3/2020
EP 3804615 A1 4/2021
EP 3875979 A1 9/2021
JP 5878009 B2 3/2016
KR 102001398 B1 7/2019
WO 2007053676 A2 5/2007
WO 2009135923 A1 11/2009
WO 2012075577 A1 6/2012
WO 2013121374 A2 8/2013
WO 2014162273 A1 10/2014
WO 2016007734 A1 1/2016
WO 2017040152 A1 3/2017
WO 2017139110 A1 8/2017
WO 2018046412 A1 3/2018
WO 2018183044 A1 10/2018
WO 2018200493 A1 11/2018
WO 2018202541 A1 11/2018
WO 2019046299 A1 3/2019
WO 2019063520 A1 4/2019
WO 2019074938 A1 4/2019
WO 2019102846 A1 5/2019
WO 2019204406 A1 10/2019
WO 2019241659 A1 12/2019
WO 2021052850 A1 3/2021
WO 2021069338 A1 4/2021
WO 2021069343 A1 4/2021
WO 2021197996 A1 10/2021

OTHER PUBLICATIONS

Baccouche; et al, "Sequential Deep Learning for Human Action Recognition", International Workshop on Human Behavior Understanding, 2011, 29-39.

Bannas; et al, "Combined Gadoxetic Acid and Gadofosveset Enhanced Liver MRI: a Feasibility and Parameter Optimization Study", Magnetic Resonance in Medicine, 2016, 75, 318-328.

Baytas Inci M.; et al, "Patient Subtyping via Time-Aware LSTM Networks", 2017.

Cannella; et al, "Common pitfalls when using the Liver Imaging Reporting and Data System (LI-RADS): lessons learned from a multi-year experience", Abdominal Imaging, Aug. 2, 2018, 43-53.

Caraiani; et al, "Description of Focal Liver Lesions With GD-EOB-DTPA Enhanced MRI", Clujul Medical, 2015, vol. 88 No. 4, 438-448.

Chiusano; et al, "DCE-MRI Analysis Using Sparse Adaptive Representations", 2011, 67-74.

Conversano; et al, "Hepatic Vessel Segmentation for 3D Planning of Liver Surgery: Experimental Evaluation of a New Fully Automatic Algorithm", Academic Radiology, Apr. 2011, vol. 18/ No. 4, 461-470.

Coulden; Richard, "State-of-the-Art Imaging Techniques in Chronic Thromboembolic Pulmonary Hypertension", Proceedings of the American Thoracic Society, 2006, vol. 3, 577-583.

Delcroix Marion; et al, "Chronic Thromboembolic Pulmonary Hypertension; Epidemiology and Risk Factors", Annals of the American Thoracic Society, Jul. 2016, vol. 13 Supp. 13, S201-S206.

"FDA Reclassification Letter regarding OsteoDetect", May 24, 2018.

Fischer; et al, "Ultra-high-field imaging of the biliary tract of 7 Tesla: initial results of Gd-EOB-DTPA-enhanced MRCP", Proc. Intl. Soc. Mag. Reson. Med., 2012, 20.

(56) References Cited

OTHER PUBLICATIONS

Frydrychowicz; et al, "Hepatobiliary MR Imaging with Gadolinium Based Contrast Agents", J Magn Reson Imaging, Mar. 2012, 35 (3), 492-511.
Galie Nazzareno; et al, "2015 ESC/ERS Guidelines for the diagnosis and treatment of pulmonary hypertension", European Heart Journal, Jan. 2016, vol. 37, Issue 1, 67-119.
Ghodasara; Satyam et al, "Quantifying Perfusion Properties with DCE-MRI Using a Dictionary Matching Approach", International Society for Magnetic Resonance in Medicine, ISMRM,, Jun. 1, 2018.
Hachulla; et al, "Dual-energy computed tomographic imaging of pulmonary hypertension", Swiss Medical Weekly, 2016, 146; w14328, 1-20.
Hope; et al, "Improvement of Gadoxetate Arterial Phase Capture With a High Spatio-Temporal Resolution Multiphase Three-Dimensional SPGR-Dixon Sequence", Journal of Magnetic Resonance Imaging, 2013, 38, 938-945.
Huang Gao.; et al, "Densely Connected Convolutional Networks", Jan. 28, 2018.
"International Preliminary Report on Patentability from PCT Application No. PCT/EP2020/075288", Mar. 31, 2022.
"International Preliminary Report on Patentability from PCT Application No. PCT/EP2020/075593", Mar. 31, 2022.
"International Preliminary Report on Patentability from PCT Application No. PCT/EP2020/077775", Apr. 12, 2022.
"International Preliminary Report on Patentability from PCT Application No. PCT/IB2020/058688", Mar. 31, 2022.
"International Preliminary Report on Patentability from PCT Application No. PCT/US2020/021861", Sep. 23, 2021.
"International Search Report and Written Opinion from PCT Application No. PCT/IB2020/058688", Dec. 9, 2020.
Ji; et al, "3D Convolutional Neural Networks for Human Action Recognition", IEEE Transactions on Pattern Analysis and Machine Intelligence, Jan. 2013, vol. 35 No. 1, 221-231.
Karpathy; et al, "Large-scale Video Classification with Convolutional Neural Networks", Proceedings of the IEEE Conference on Computer Vision and Pattern Recognition, 2014, 1725-1732.
Khan; et al, "Chapter 3.3 "Neural Networks Basics"", A Guide to Convolutional Neural Networks for Computer Vision, Morgan & Claypool Publishers, 2018, pp. 36-39.
Kim; et al, "Arterial subtraction images of gadoxetate-enhanced MRI improve diagnosis of early-stage hepatocellular carcinoma", Journal of Hepatology, 2019, vol. 71, 534-542.
kim; et al, "Gadoxetic acid-enhanced magnetic resonance imaging: Hepatocellular carcinoma and mimickers", Clinical and Molecular Hepatology, Sep. 2019, vol. 25 No. 3, 223-233.
Knobloch; et al, "Combined Gadoxetic Acid and Gadobenate Dimeglumine Enhanced Liver MRI for Liver Metastasis Detection: a Parameter Optimization Study", Proc. Intl. Soc. Mag. Reson. Med., 2018.
Kwon; et al, "Differentiation of small (less than or equal to cm) hepatocellular carcinomas from small benign nodules In cirrhotic liver on gadoxetic acid-enhanced and diffusion-weighted magnetic resonance images", Abdominal Imaging, Jul. 6, 2014, pp. 64-78.
Le; Quoc V., "A Tutorial on Deep Learning Part 2: Autoencoders, Convolutional Neural Networks and Recurrent Neural Networks", Oct. 20, 2015.
Marcan; et al, "Segmentation of hepatic vessels from MRI images for planning of electroporation-based treatments in the liver", Radiol. Oncol., 2014, 48 (3), 267-281.
Meng Qinxue; et al, "Relational Autoencoder for Feature Extraction", Feb. 9, 2018.
Moccia; et al, "Blood vessel segmentation algorithms—Review of methods, datasets and evaluation metrics", Computer Methods and Programs in Biomedicine, 2018, 158, 71-91.
Shtern; Alon, "Shape Correspondence Using Spectral Methods and Deep Learning Research Thesis", Aug. 2017.
Simonyan; et al, "Two-Stream Convolutional Networks for Action Recognition in Videos", Advances in Neural Information Processing Systems, 2013, 568-576.
Smith; Dana, "Artificial Intelligence Can Detect Alzheimer's Disease in Braine Scans Six Years Before a Diagnosis", Jan. 2, 2019.
Tapson Victor; et al, "Incidence and Prevalence of Chronic Thromboembolic Pulmonary Hypertension", Proceedings of the American Thoracic Society, Sep. 7, 2006, vol. 3, 564-567.
Thompson; et al, "Indicator Transit Time Considered as a Gamma Variate", Circulation Research, Jun. 1964, vol. XIV, 502-515.
Wang; et al, "Stacked Fully Convolutional Networks for Pulmonary Vessel Segmentation", IEEE Visual Communications and Image Processing (VCIP), 2018.
Weizman; et al, "Prediction of Brain MR Scans in Longitudinal Tumor Follow-up Studies", Oct. 1, 2012, pp. 179-187.
Chibuzo; Abonyi et al, "Intravascular Contrast Media in Radiography: Historical Development Review of Risk Factors for Adverse Reactions", South American Journal of Clinical Research, 2016, Vo. 3, Issue 1.
Ignee; Andre et al, "Ultrasound contrast agents", Endoscopic Ultrasound, Nov.-Dec. 2016, vol. 5, Issue 6, 355-362.
Karani Neerav et al: "Temporal Interpolation of Abdominal MRIs Acquired During Free-Breathing", 4. Sep. 2017 (Sep. 4, 2017), 12th European Conference on Computer Vision, ECCV 2012; [Lecture Notes in Computer Science], Springer Berlin Heidelberg, Berlin, Heidelberg, pp. 359-367, XP047528114, ISSN: 0302-9743 ISBN: 978-3-642-39453-9.
Lusic Hrvoje; et al, "X-Ray Computed Tomography Contrast Agents", Chem. Rev., 2013.
Nouh Mohamed; et al, "Radiographic and magnetic resonances contrast agents: Essentials and tips for safe practices", World Journal of Radiology, Sep. 28, 2017, vol. 9, Issue 9, 339-349.
Qin Chen et al: "Convolutional Recurrent Neural Networks for Dynamic MR Image Reconstruction", IEEE Transactions on Medical Imaging, IEEE Service Center, Piscataway, NJ, US, Bd. 38, Nr. 1, 1. Jan. 2019 (Jan. 1, 2019), Seiten 280-290, P011694961, ISSN: 0278-0062, DOI: 10.1109/TMI.2018.2863670.
Smits Loek; et al, "Evaluation of ultrasmall superparamagnetic iron oxide (USPIO) enhanced MRI with ferumoxytol to quantify arterial wall inflammation", Atherosclerosis, 2017, 263, 211-218.
Takeshima, Hidenori: "Integrating Spatial and Temporal Correlations into a Deep Neural Network for Low-delay Reconstruction of Highly Undersampled Radial Dynamic Images", International Society for Magnetic Resonance in Medicine, ISMRM, 2030 Addison Street, 7th Floor, Berkeley, CA 94704 USA, pp. 2796, Jun. 1, 2018 (Jun. 1, 2018).
"Written Opinion from PCT Application No. PCT/EP2021/057689", Jun. 24, 2021.
Xiao; Yu-Dong et al, "MRI contrast agents: Classification and application (Review)", International Journal of Molecular Medicine, 2016, 38, 1319-1326.
He, et al., "Deep Predictive Modeling of Dynamic Contrast-Enhanced MRI Data", Proc. Intl. Soc. Mag. Reson. Med., 2019, vol. 27.
Kurozumi, et al., "Evaluation of hemodynamic imaging findings of hypervascular hepatocellular carcinoma: comparison between dynamic contrast-enhanced magnetic resonance imaging using radial volumetric imaging breath-hold examination with k-space-weighted image contrast reconstruction and dynamic computed tomography during hepatic arteriography", Japanese Journal of Radiology, 2018, pp. 295-302, vol. 36.
Zhang, et al., "Dynamic contrast enhanced MR imaging for evaluation of angiogenesis of hepatocellular nodules in liver cirrhosis in N-nitrosodiethylamine induced rat model", Eur. Radiol., 2017, pp. 2086-2094, vol. 27.
Yasaka, et al., "Liver Fibrosis: Deep Convolutional Neural Network for Staging by Using Gadoxetic Acid-enhanced Hepatobiliary Phase MR Images", Dec. 14, 2017, Radiology, vol. 287, No. 1.
Bellani; Giacomo et al, "Epidemiology, Patterns of Care, and Mortality for Patients With Acute Respiratory Distress Syndrome in Intensive Care Unites in 50 Countries", JAMA, 2016.

(56) References Cited

OTHER PUBLICATIONS

Choi; Jun-Ho et al, "EmbraceNet: a robust deep learning architecture for multimodal classification", Information Fusion, 2019, 51, 259-270.
Gong Enhao; et al, "Deep Learning Enables Reduced Gadolinium Dose for Contrast-Enhanced Brain MRI", J. Magn. Reson. Imaging, 2018, 48, 330-340.
"Information on Primovist", 2016.
"International Preliminary Report on Patentability from PCT Application No. PCT/EP2020/077767", Apr. 12, 2022.
"Introduction to Multimodal Learning Model", DEV Community, Feb. 5, 2019.
Rajpurkar; Pranav et al, "CheXNet: Radiologist-Level Pneumonia Detection on Chest X-Rays with Deep Learning", 2017.
Yasaka Koichiro; et al, "Deep Learning with Convolutional Neural Network for Differentiation of Liver Masses at Dynamic Contrast-enhanced CT: a Preliminary Study", Radiology, Mar. 2018, vol. 286; No. 3, 887-896.

* cited by examiner

ASSISTANCE IN THE DETECTION OF PULMONARY DISEASES

CROSS REFERENCE TO RELATED APPLICATIONS

The present application is a U.S. national stage filing under 35 U.S.C. § 371 of International Application No. PCT/EP2020/083003, filed 23 Nov. 2020, which claims priority to European Patent Application No. EP 19213939.2, filed 5 Dec. 2019, and European Patent Application No. EP 20151108.6, filed 10 Jan. 2020, the disclosures of each of which are incorporated in their entirety herein by this reference.

The present disclosure relates to the detection of acute respiratory distress syndrome in a patient. Subjects of the present disclosure are a computer system, a method and a computer program product for detection of acute respiratory distress syndrome.

Acute respiratory distress syndrome (ARDS) is a life-threatening disease in which the lungs cannot work properly. ARDS is caused by damage in the capillary wall that can be attributed to a disease or physical injury. This damage makes the capillary wall leaky, which leads to an accumulation of fluid and ultimately to the collapse of the alveoli. As a result, the lungs are no longer capable of exchanging oxygen and carbon dioxide. ARDS does not usually occur as an independent disease, but is the result of another disease or a severe accident or injury.

Although every tenth intensive care patient suffers from acute respiratory distress syndrome, this life-threatening complication is frequently not detected (JAMA 2016; 315: 788-800). Impending death can frequently be prevented through a number of simple interventions; they include early mechanical ventilation with positive end-expiratory pressure (PEEP) and a reduced tidal volume. A prone position of the patient is also recommended. In clinical studies, these measures distinctly reduced mortality in some cases. However, these recommendations can only be implemented if ARDS is detected early.

There are numerous publications on the automatic detection of lung diseases on the basis of patient data. P. Rajpurkar et al., describe an artificial neural network for detection of pneumonia on the basis of chest X-rays of patients (CheXNet: *Radiologist-Level Pneumonia Detection on Chest X-Rays with Deep Learning*; arXiv: 1711.05225 [cs.CV]). However, ARDS cannot be reliably detected from X-rays alone. WO2013/121374 A2 discloses a system for detection of ARDS in a patient that analyzes physiological parameters of the patient. However, physiological parameters alone do not allow reliable detection of ARDS.

Proceeding from the prior art described, it is an object of the present disclosure to provide a solution for reliable detection of ARDS in intensive care patients.

This object is achieved by the subjects of the independent claims. Preferred embodiments can be found in the dependent claims and also in the present description and the drawings.

The present disclosure provides in a first aspect a computer system comprising an input unit, a control and calculation unit and an output unit wherein the control and calculation unit is configured to prompt the input unit to receive patient data relating to an intensive care patient, wherein the patient data comprise at least the following patient data:

a plurality of radiological images of the thorax of the intensive care patient, wherein the radiological images show the thorax at different times, and a plurality of vital data relating to vital parameters of the intensive care patient, wherein the vital data specify values relating to the vital parameters at different times, wherein the control and calculation unit is configured to supply the received patient data to an artificial neural network, wherein the artificial neural network comprises at least three subnetworks, a first subnetwork, a second subnetwork and a third subnetwork, wherein the first subnetwork comprises a first input layer, wherein the second subnetwork comprises a second input layer, wherein the third subnetwork comprises an output layer, and wherein the first subnetwork and the second subnetwork are merged in the third subnetwork, wherein the plurality of radiological images is supplied to the first input layer and the plurality of vital data is supplied to the second input layer, wherein the first subnetwork is configured to generate a time-dependent image descriptor for each radiological image, wherein the second subnetwork is configured to generate time-dependent vital data descriptors from the vital data, wherein the time-dependent image descriptors and the time-dependent vital data descriptors are supplied to layers in the artificial neural network that comprise feedback neurons, wherein the artificial neural network has been trained using reference data to calculate an ARDS indicator value on the basis of patient data and to output the ARDS indicator value via the output layer, wherein the control and calculation unit is configured to receive the ARDS indicator value from the artificial neural network, wherein the control and calculation unit is configured to compare the ARDS indicator value with a threshold value, and wherein the control and calculation unit is configured to prompt the output unit to output a notification if the ARDS indicator value deviates from the threshold value in a defined manner.

The present disclosure further provides a method for detecting ARDS in an intensive care patient, comprising the steps of receiving patient data relating to the intensive care patient, wherein the patient data comprise at least the following patient data:

a plurality of radiological images of the thorax of the intensive care patient, wherein the radiological images show the thorax at different times, and a plurality of vital data relating to vital parameters of the intensive care patient, wherein the vital data specify values relating to the vital parameters at different times, supplying the patient data to an artificial neural network, wherein the artificial neural network comprises at least three subnetworks, a first subnetwork, a second subnetwork and a third subnetwork, wherein the first subnetwork comprises a first input layer, wherein the second subnetwork comprises a second input layer, wherein the third subnetwork comprises an output layer, and wherein the first subnetwork and the second subnetwork are merged in the third subnetwork, wherein the plurality of radiological images is supplied to the first input layer and the plurality of vital data is supplied to the second input layer, wherein the first subnetwork is configured to generate a time-dependent image descriptor for each radiological image, wherein the second subnetwork is configured to generate time-dependent vital data descriptors from the vital data, wherein the time-dependent image descriptors and the time-dependent vital data descriptors are supplied to layers in the artificial neural network that comprise feedback neurons, wherein the artificial neural network has been trained using reference data to calculate an ARDS indicator value on the basis of patient data and to output the ARDS indicator value via the output layer, receiving an ARDS indicator value for the supplied patient data from the artificial neural network, comparing the ARDS indicator value with a threshold value, outputting a notification if the ARDS indicator value deviates from the threshold value in a defined manner.

The present disclosure further provides a computer program product comprising a computer program which can be loaded into a memory of a computer system, where it prompts the computer system to execute the following steps:

receiving patient data relating to the intensive care patient, wherein the patient data comprise at least the following patient data:

a plurality of radiological images of the thorax of the intensive care patient, wherein the radiological images show the thorax at different times, and a plurality of vital data relating to vital parameters of the intensive care patient, wherein the vital data specify values relating to the vital parameters at different times, supplying the patient data to an artificial neural network, wherein the artificial neural network comprises at least three subnetworks, a first subnetwork, a second subnetwork and a third subnetwork, wherein the first subnetwork comprises a first input layer, wherein the second subnetwork comprises a second input layer, wherein the third subnetwork comprises an output layer, and wherein the first subnetwork and the second subnetwork are merged in the third subnetwork, wherein the plurality of radiological images is supplied to the first input layer and the plurality of vital data is supplied to the second input layer, wherein the first subnetwork is configured to generate a time-dependent image descriptor for each radiological image, wherein the second subnetwork is configured to generate time-dependent vital data descriptors from the vital data, wherein the time-dependent image descriptors and the time-dependent vital data descriptors are supplied to layers in the artificial neural network that comprise feedback neurons, wherein the artificial neural network has been trained using reference data to calculate an ARDS indicator value on the basis of patient data and to output the ARDS indicator value via the output layer, receiving an ARDS indicator value for the supplied patient data from the artificial neural network, comparing the ARDS indicator value with a defined threshold value, outputting a notification if the ARDS indicator value deviates from the threshold value in a defined manner.

The disclosure will be more particularly elucidated below without distinguishing between the subjects of the disclosure (computer system, method, computer program product). The elucidations that follow shall instead apply analogously to all subjects of the disclosure, regardless of the context in which they are made (computer system, method, computer program product).

Where steps are listed in a specific order in the present description, this does not necessarily mean that the steps must also be performed in the order specified. The disclosure shall instead be understood to mean that the steps listed in a specific order can be performed in any order or else in parallel with one another, unless one step is based on another step, which will be clear in each case from the description of the steps. The orders specifically listed in this document are therefore only preferred embodiments of the disclosure.

The present disclosure provides a physician and/or hospital staff with means which assist the physician and/or the hospital staff in detecting the onset of acute respiratory distress syndrome (ARDS) in an intensive care patient.

In this connection, the physician and/or the hospital staff is/are assisted by a computer system.

A "computer system" is an electronic data processing system that processes data by way of programmable computing rules. Such a system usually comprises a "computer", the unit that comprises a processor for performing logic operations, and also peripherals.

In computer technology, "peripherals" refers to all devices that are connected to the computer and are used for control of the computer and/or as input and output devices. Examples thereof are monitor (screen), printer, scanner, mouse, keyboard, drives, camera, microphone, speaker and the like. Internal ports and expansion cards are also regarded as peripherals in computer technology.

Modern computer systems are frequently divided into desktop PCs, portable PCs, laptops, notebooks, netbooks, tablet PCs, handhelds (e.g., smartphones), cloud computers and workstations; all these systems can in principle be utilized for execution of the disclosure. Preferably, the present disclosure is executed on one or more computer systems in hospital intensive care units. It is conceivable for such a computer system to execute further functions in an intensive care unit, such as, for example, monitoring the state of health of intensive care patients. Preferably, the computer system can access databases of the hospital, in which patient data of the intensive care patients can be stored. Preferably, the disclosure is executed automatically on one or more computer systems as a background process.

The computer system according to the disclosure is configured to determine an ARDS indicator value on the basis of patient data. The ARDS indicator value correlates with the probability of acute respiratory distress syndrome being present in the intensive care patient. Preferably, the ARDS indicator value specifies the probability of ARDS being present in the intensive care patient, wherein a value of 0 can mean that ARDS can be ruled out and a value of 1 or 100% can mean that all evaluated patient data indicate and/or infer that ARDS is present.

The computer system according to the disclosure is configured to compare the ARDS indicator value with a defined threshold value. If there is a defined deviation between the ARDS indicator value and the threshold value, the computer system outputs a notification. Preferably, the computer system according to the disclosure is configured to output a notification if the ARDS indicator value is above the defined threshold value, the probability of ARDS being present in the intensive care patient thus exceeding the threshold value. In such a case, measures preventing deterioration of the patient's condition should be taken. If the ARDS indicator value is below the defined threshold value, the probability of ARDS being present in the intensive care patient is sufficiently low for no ARDS-specific measures to be necessary.

The threshold value can be, for example, a value between 0.5 (or 50%) and 1. Preferably, the threshold value is defined by a physician and/or on the basis of medical experience, in particular on the basis of experience that can be gained by means of the present disclosure. For example, the threshold value can deliberately be set low to begin with in order to rule out any risk of overlooking acute respiratory distress syndrome in a patient. The threshold value can then be adjusted over time to a higher threshold value that seems appropriate from a medical perspective and medical experience.

The notification can be an on-screen notification (e.g., a text message) and/or an audible signal and/or a visual signal and/or a vibrating alert and/or the like. The notification can be output on one or more output units of the computer system according to the disclosure, for example displayed on a monitor and/or output via a speaker and/or output on a printer, for example as a text message, and/or transmitted, for example, via e-mail to a stationary computer system or a mobile receiving device (e.g., a smartphone or a tablet computer or a pager).

The notification is intended to prompt a physician and/or hospital staff to attend to the intensive care patient and to take measures to prevent deterioration of the patient's state of health. Preferably, the notification comprises recommended actions to be taken by a physician or hospital staff in order to prevent deterioration of the state of health of the intensive care patient.

The computer system according to the disclosure is configured to automatically determine the ARDS indicator value, to automatically compare the ARDS indicator value with the defined threshold value and to automatically send one or more notifications.

"Automatically" means that no human intervention at all is required.

The ARDS indicator value is determined on the basis of patient data. The computer system according to the disclosure can have access to the patient data and/or the patient data can be automatically supplied to the computer system.

The patient data can be present, for example, in one or more data storage media that are part of the computer system according to the disclosure or are connected thereto via a network or via multiple networks. In particular, such data storage media can be one or more databases of a hospital, preferably databases in which patient data are stored. The computer system according to the disclosure can be configured to read patient data from the one or more data storage media at defined times and/or at defined time intervals and/or upon occurrence of defined events (e.g., when new patient data become available) and to use said patient data to determine the ARDS indicator value.

It is also conceivable that the computer system according to the disclosure is configured to retrieve/receive patient-specific data from medical devices and/or computer systems connected to medical devices.

The term "medical devices" is understood to mean devices that can be used to obtain physiological information about a patient. Examples of such medical devices are heart rate monitors, blood pressure monitors, clinical thermometers, X-ray machines, computed tomography machines and the like. The medical devices are, in particular, X-ray machines, computed tomography machines, ventilators and devices which can be used to determine the value for partial pressure of arterial oxygen $PaO_2$ of a patient, the value for concentration of inspired oxygen $FiO_2$ and/or the $PaO_2/FiO_2$ ratio and also values for PEEP and CPAP (PEEP=positive end-expiratory pressure; CPAP=continuous positive airway pressure).

Preferably, the computer system according to the disclosure is configured to determine an ARDS indicator value whenever new patient data are acquired and are stored in a data storage medium which can be part of the computer system according to the disclosure or to which the computer system according to the disclosure can be connected. The computer system according to the disclosure can be configured to check at defined time intervals (e.g., every 10 minutes) whether new patient data are present in the data storage medium.

The patient data, which are used to determine the ARDS indicator value, comprise a plurality of radiological images of the thorax of the intensive care patient.

Examples of radiological images are x-rays, CT scans (CT=computed tomography) and the like. Preference is given to using X-rays. In ARDS patients, bilateral compressions in the lungs can, for example, be seen in radiological images (see, for example, H. M. Kulke: *Röntgendiagnostik von Thoraxerkrankungen* [X-ray diagnosis of thoracic diseases], De Gruyter Verlag 2013, ISBN 978-3-11-031118-1).

The individual radiological images show the thorax of the intensive care patient at different times. Preferably, at least three images generated within the last seven days are present. Particularly preferably, the most recent radiological image was generated within the last 24 hours, even more preferably within the last 12 hours, most preferably within the last three hours.

Preferably, the radiological images each bear a timestamp indicating when they were generated (captured by measurement).

The radiological images are preferably present as digital image files. The term "digital" means that the radiological images can be processed by a machine, generally a computer system. "Processing" is understood to mean the known methods for electronic data processing (EDP).

Digital image files can be present in various formats. For example, digital image files can be coded as raster graphics. Raster graphics consist of a grid arrangement of so-called picture elements (pixel) or volume elements (voxel), to which a color or a gray value is assigned in each case. For the sake of simplicity, it is assumed in this description that the radiological images are present as raster graphics.

However, this assumption is not to be understood as limiting in any way. There are a multitude of possible digital image formats and color codings; for a person skilled in the art in image processing, it is clear how the teaching in this description can be applied to different image formats.

Further patient data used to determine an ARDS indicator value comprise vital data relating to vital parameters of the intensive care patient.

"Vital parameters" are measured values of important bodily functions that are established when checking vital signs. Vital parameters usually encompass the heart rate, the respiratory rate, the blood pressure and the body temperature of the intensive care patient.

Further vital parameters are blood oxygen saturation and/or partial pressure of oxygen.

Oxygen saturation, $sO_2$ for short, is the quotient of the oxygen present in the blood and the maximum oxygen capacity of the blood in percent. Oxygen saturation thus indicates what percentage of the total hemoglobin in the blood is loaded with oxygen. Oxygen saturation can be determined in various sections of the cardiovascular system using different methods. A distinction can be made between the following oxygen saturations: arterial oxygen saturation ($S_aO_2$), venous oxygen saturation ($S_vO_2$), central venous oxygen saturation ($S_{ev}O_2$) and mixed venous oxygen saturation ($S_{mv}O_2$) Preferably, arterial oxygen saturation and/or mixed venous oxygen saturation is/are measured. Oxygen saturation is preferably measured using a pulse oximeter and/or by blood gas analysis.

The partial pressure of oxygen ($pO_2$) refers to the pressure exerted by the gaseous oxygen in the blood. The higher the partial pressure of oxygen in the blood, the higher the oxygen saturation. This relationship is nonlinear because the oxygen affinity of hemoglobin is dependent on the number of $O_2$ molecules already bound; the oxygen binding curve shows an s-shaped curve. Preferably, the partial pressure of oxygen ($p_aO_2$) is measured.

A further vital parameter is the fraction of inspired oxygen ($FiO_2$). The fraction of inspired oxygen indicates the proportion of oxygen in the inspired gas. It can be specified as a percentage or as a decimal number.

A further vital parameter is the oxygenation index (Horowitz quotient). It is defined as the quotient of the partial pressure of arterial oxygen ($p_aO_2$) and the concentration of oxygen in the inspired air ($FiO_2$): Horowitz quotient=$p_aO_2/FiO_2$.

Further vital parameters are conceivable, in particular vital parameters that can be calculated or derived from the vital parameters stated.

Since a blood gas analysis is regularly carried out for intensive care patients, further values of parameters determined during the blood gas analysis can be included as vital parameters in the automatic detection of ARDS, such as, for example, the pH of the blood, the partial pressure of carbon dioxide, actual bicarbonate, excess base and/or the like (see, for example, H. W. Striebel: Anästhesie, Intensivmedizin, Notfallmedizin [Anesthesia, intensive care, emergency care], 7th edition, Schattauer 2009, ISBN: 978-3-7945-2635-2). The same applies to further parameters, the values of which are routinely determined for intensive care patients.

The vital data describe the values of the vital parameters at different times. Values of at least ten particular times, preferably generated within the last 12 hours, are preferably available for each vital parameter. In one embodiment, the vital data each bear a timestamp indicating when they were acquired. In another embodiment, the vital data or part of the vital data are temporal profile data, i.e., values of vital parameters as a function of time.

It is conceivable for further data to be taken as a basis for determination of the ARDS indicator value. Said further data can be dynamic data. The term "dynamic data" is understood to mean data that can change significantly over a period of time (e.g., within a week or within a day). Dynamic data include the vital data described. The further data can also be quasi-static and/or static data. This is understood to mean data that do not change significantly (quasi-statically) or do not change at all (statically) over the period of time. A "significant change" is present if the change is of significance for the course of the disease, in particular the possible occurrence of ARDS. An example of a static datum is the sex of the intensive care patient. An example of a quasi-static datum is the age or the weight or the height of the intensive care patient. The further data can also be historical data, such as, for example, the result of a diagnosis, anamnesis data, data relating to the self-assessment by the patient, and the like.

The ARDS indicator value is determined with the aid of an artificial neural network. The artificial neural network has been trained using reference data to determine an ARDS indicator value on the basis of patient data. The artificial neural network can have been trained and validated by means of supervised learning, for example. In this case, patient data were presented to the artificial neural network, and it was communicated to the artificial neural network whether the patients from whom the patient data originate are suffering from ARDS or are not suffering from ARDS. This training data can be used, for example, to create a model by means of a backpropagation process, which model learns a relationship between the patient data and the diagnosis (ARDS is present or is not present), which relationship can be applied to unknown patient data (data from patients for whom it is not exactly known whether they are suffering from ARDS).

The artificial neural network according to the disclosure comprises separate input layers for the radiological images and for the vital data. Accordingly, at least two input layers are present, a first input layer for the input of the radiological images and a second input layer for the vital data. It is also conceivable that more than two input layers are present. For example, it is conceivable that a separate input layer is present for each radiological image of the present plurality of radiological images. It is also conceivable that, for each vital parameter measured, a separate input layer for the corresponding vital data is present. It is also conceivable that further input layers are present for further data, for example for further dynamic, quasi-static and/or static data.

At least the radiological images and the vital data are initially processed separately from one another by the artificial neural network according to the disclosure. The aim of this separate processing is to determine separate time-dependent descriptors. The artificial neural network according to the disclosure therefore comprises at least three subnetworks, a first subnetwork, a second subnetwork and a third subnetwork. The first subnetwork is used to determine time-dependent descriptors for the radiological images. Said descriptors are also referred to as image descriptors in this description. The second subnetwork is used to determine time-dependent descriptors for the vital data. Said descriptors are also referred to as vital data descriptors in this description. The first subnetwork and the second subnetwork are merged in the third subnetwork. Merging is understood to mean that at least one layer of the first subnetwork and at least one layer of the second subnetwork are respectively connected to a layer of the third subnetwork. The third subnetwork comprises an output layer. The output layer is used to output the ARDS indicator value.

The image descriptors and the vital data descriptors are each representations of the respective data. An image descriptor is a representation of a radiological image; a vital data descriptor is a representation of values of one or more vital parameters. The descriptor preferably has fewer dimensions than the original data. When a descriptor is generated, what is thus generated is a representation of the respective data that manages with fewer dimensions than the original data. This dimensionality reduction can be achieved, for example, by a convolutional neural network (CNN). Accordingly, the first and/or the second subnetwork can each be constructed as a CNN or comprise relevant layers (in particular convolutional layers and pooling layers).

The first subnetwork for generation of the image descriptors is preferably a dense convolutional network (DenseNet). Such networks are described, for example, in: G. Hunag et al., *Densely Connected Convolutional Networks*, arXiv: 1608.06993v5 [cs.CV] 28 Jan. 2018. The ChestXNet already mentioned above or parts thereof can also be used as the first subnetwork.

The image descriptors and the vital data descriptors are time-dependent descriptors. This means that the information on the times at which the data underlying the descriptor were acquired is still present in the descriptor at least in part or is added to said descriptor during further processing thereof by the artificial neural network according to the disclosure. This time information is important for the determination of the ARDS indicator value and is processed by feedback neurons. The artificial neural network according to the disclosure accordingly has feedback neurons. In particular, the third subnetwork comprises a recurrent (feedback) neural subnetwork. The artificial neural network according to the disclosure is thus capable of taking into account the development over time for both the radiological images and the vital data when determining the ARDS indicator value.

A particularly suitable recurrent network is a long short-term memory (LSTM) or a time-aware LSTM network (see, for example, I. M. Baytas et al., Patient Subtyping via Time Aware LSTM Networks, Proceedings of KDD '17, 2017, DOI:10.1145/3097983.3097997).

In a preferred embodiment, the third subnetwork has feedback neurons. The first and/or, in particular, the second subnetwork can likewise have feedback neurons.

In a preferred embodiment, the second subnetwork has an autoencoder and/or it has been pretrained with the aid of an autoencoder. The aim of an autoencoder is to learn a compressed representation (encoding) for a set of data and to thus also extract essential features. This means that it can be used for dimensionality reduction. Autoencoders are described, for example, in Q. V. Le: *A Tutorial on Deep Learning Part 2: Autoencoders, Convolutional Neural Networks and Recurrent Neural Networks,* 2015, https://cs.stanford.edu/~quocle/tutorial2.pdf; W. Meng: Relational Autoencoder for Feature Extraction, arXiv: 1802.03145v1 [cs.LG] 9 Feb. 2018; WO2018046412 A1.

In a particularly preferred embodiment, the second subnetwork comprises a recurrent (feedback) neural network followed by an autoencoder.

The disclosure is more particularly elucidated below with reference to figures, without wishing to restrict the disclosure to the features or combinations of features that are shown in the figures.

FIG. 1 shows schematically one embodiment of the computer system (10) according to the disclosure. The computer system (10) comprises an input unit (11), a control and calculation unit (12) and an output unit (13). The control and calculation unit (12) comprises a processing unit (14) having one or more processors for performing logical operations and a memory unit (15).

Patient data are received and/or retrieved via the input unit (11).

The processing unit (14) is configured with processor-executable instructions (which can be stored in the memory unit (15)) to determine an ARDS indicator value on the basis of the patient data with the aid of an artificial neural network (which can likewise be stored in the memory unit (15)) and to compare said ARDS indicator value with a threshold value. The processing unit (14) is also configured to output a notification via the output unit (13) upon a defined deviation of the ARDS indicator value from the threshold value.

Figure 2:
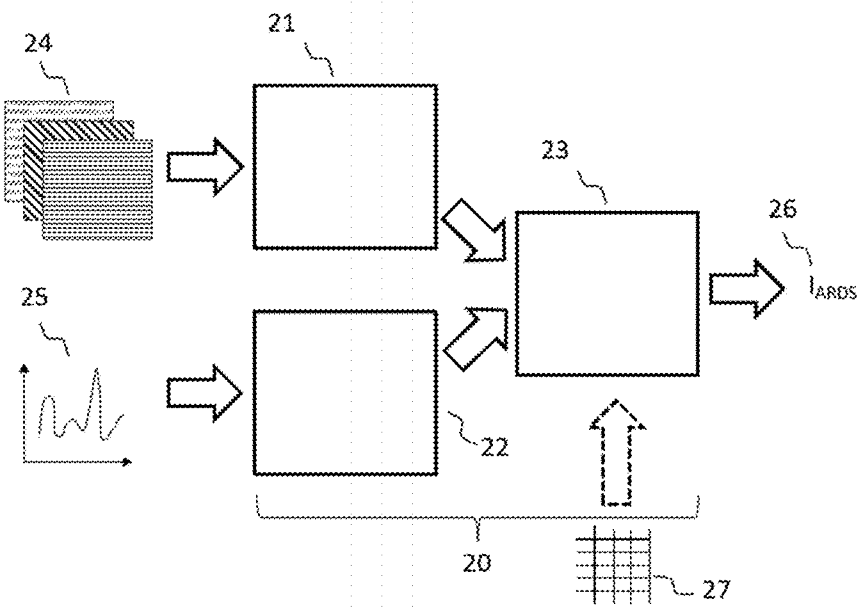

FIG. 2 shows schematically one embodiment of the neural network (20) according to the disclosure. The network (20) comprises a first subnetwork (21), a second subnetwork (22) and a third subnetwork (23). Radiological images (24) of an intensive care patient are supplied to the first subnetwork (21). Vital data (25) of vital parameters are supplied to the second subnetwork (22). The first subnetwork (21) and the second subnetwork (22) are merged in the third subnetwork (23). An ARDS indicator value (26) determined by the neural network (20) on the basis of the supplied data is output via the third subnetwork (23).

It is conceivable that the neural network (20) is supplied with further data (27) that are taken into account when determining the ARDS indicator value.

Figure 3:
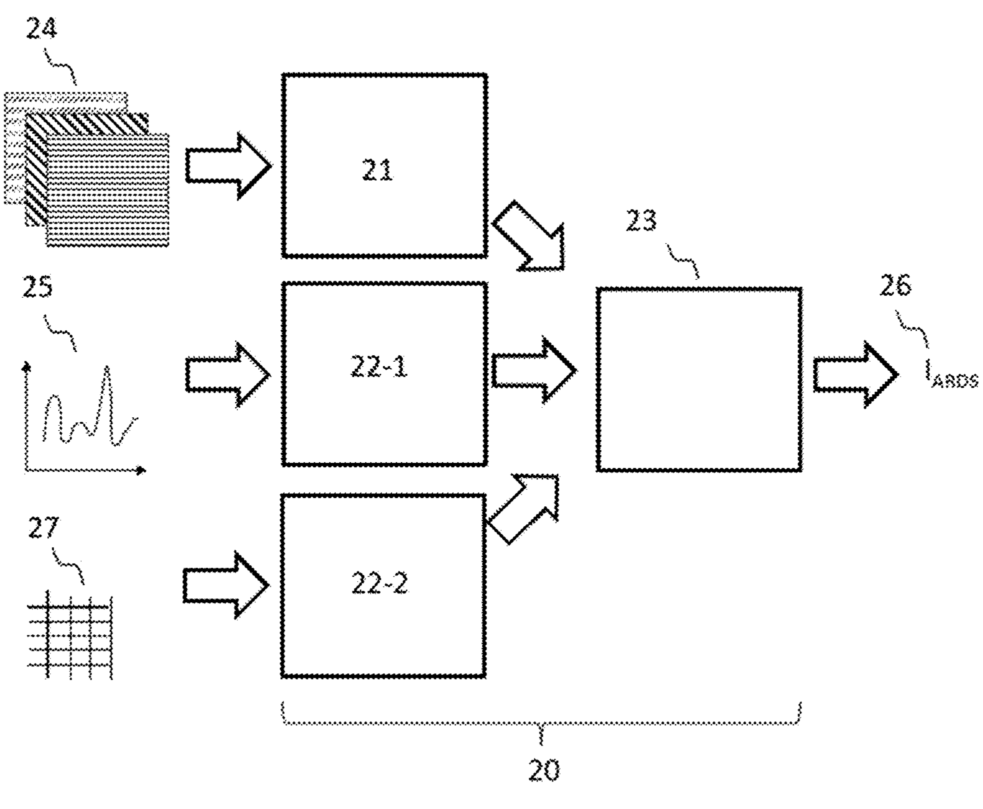

FIG. 3 shows schematically a further embodiment of the neural network (20) according to the disclosure. The network (20) comprises a first subnetwork (21), two second subnetworks (22-1, 22-2) and a third subnetwork (23). Radiological images (24) of an intensive care patient are supplied to the first subnetwork (21). Vital data (25) of vital parameters are supplied to one of the second subnetworks (22-1). Further patient data (27) are supplied to the other of the second subnetworks (22-2). The first subnetwork (21) and the second subnetworks (22-1, 22-2) are merged in the third subnetwork (23). An ARDS indicator value (26) determined by the neural network (20) on the basis of the supplied data is output via the third subnetwork (23).

Figure 4:
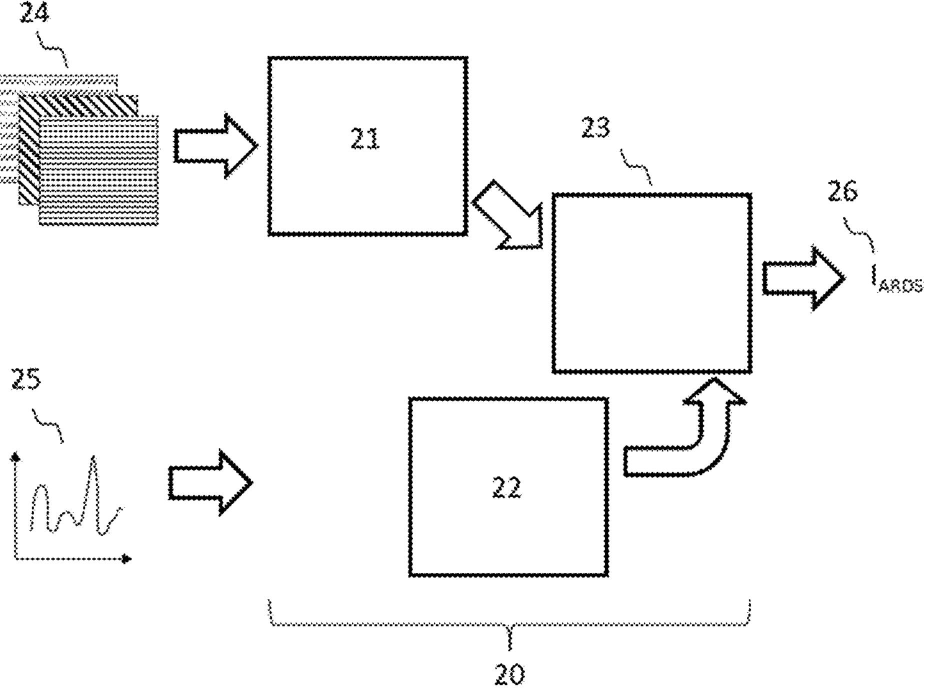

FIG. 4 shows schematically a further embodiment of the neural network (20) according to the disclosure. The network (20) comprises a first subnetwork (21), a second subnetwork (22) and a third subnetwork (23). Radiological images (24) of an intensive care patient are supplied to the first subnetwork (21). Vital data (25) of vital parameters are supplied to the second subnetwork (22). The first subnetwork (21) and the second subnetwork (22) are merged in the third subnetwork (23). An ARDS indicator value (26) determined by the neural network (20) on the basis of the supplied data is output via the third subnetwork (23).

Figure 5:
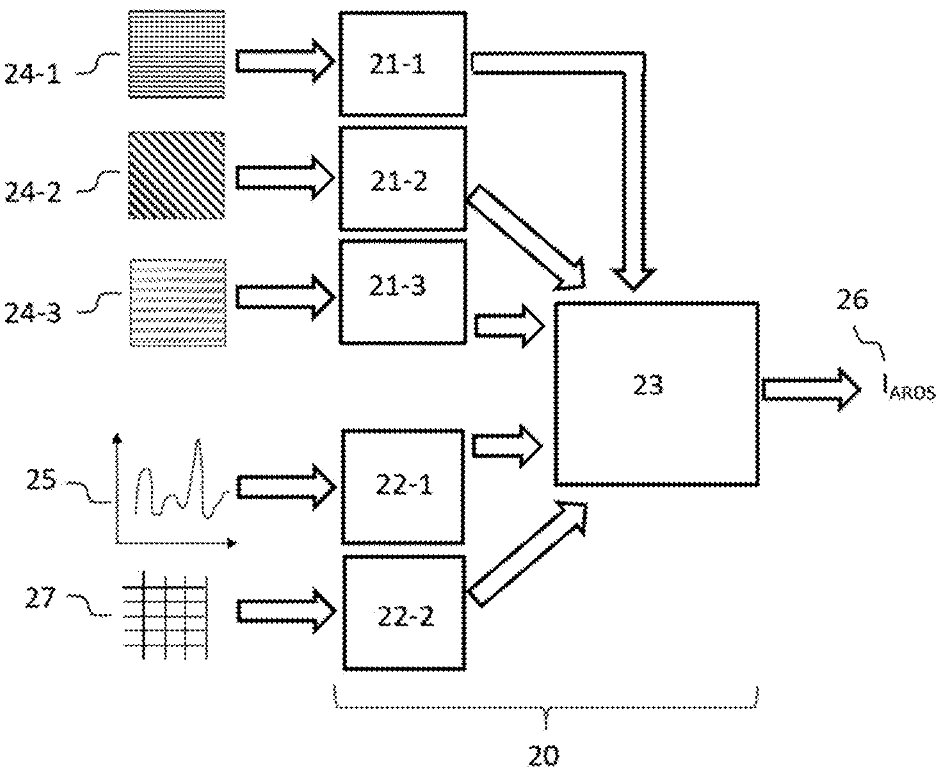

FIG. 5 shows schematically a further embodiment of the neural network (20) according to the disclosure. In the present example, multiple first subnetworks (21-1, 21-2, 21-3) are present, each subnetwork respectively processing a radiological image (24-1, 24-2, 24-3). The radiological images originate from the same patient, but were preferably recorded at different times. Preferably, the structures and weights of the first subnetworks are identical. Furthermore, multiple second subnetworks (22-1, 22-2) are present, one for processing of vital data (25) relating to vital parameters and another for processing of further data (27). Preferably, the structures and/or the weights of the second subnetworks are not identical. The subnetworks are merged in a third subnetwork (23). An ARDS indicator value (26) is output via the third subnetwork (23).

Figure 6:
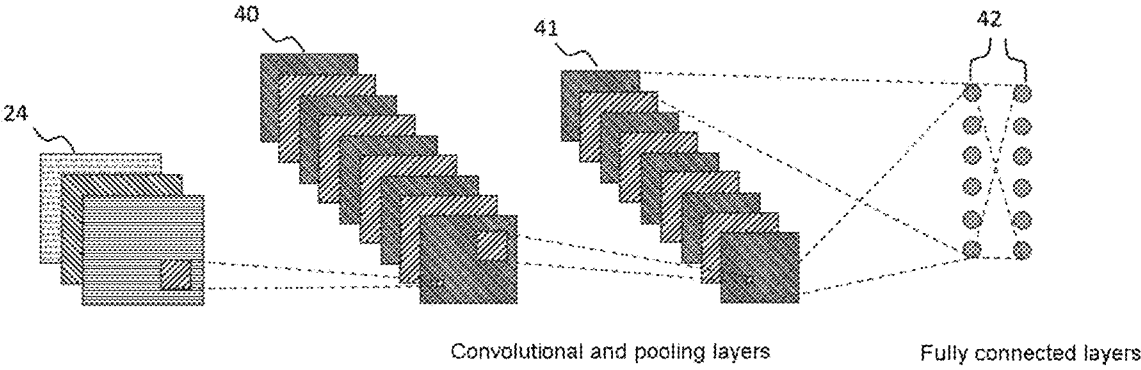

FIG. 6 shows, by way of example and schematically, the functional principle of the first subnetwork for processing of radiological images, the first subnetwork being in the form of a CNN. FIG. 6 depicts various layers within a CNN. Radiological images (24) are supplied to the CNN. For example, the gray levels of a raster graphic can be supplied pixel-by-pixel or voxel-by-voxel to an input layer as input data. The CNN usually comprises a multiplicity of convolutional layers and pooling layers (40, 41). What are performed within these layers are convolutional operations, the output of which is passed to the next layer. The dimensionality reduction performed within the convolutional layers is an aspect that enables the CNN to scale large images. The output of the convolutional and pooling layers usually ends in a plurality of fully connected layers (42).

Figure 7:
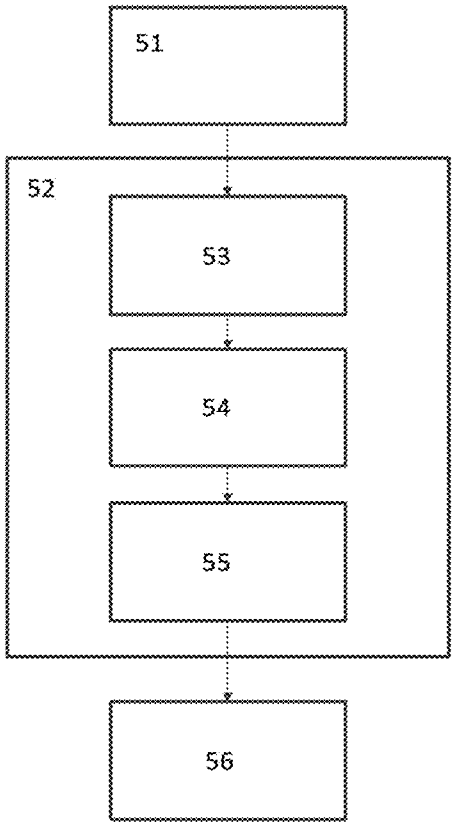

FIG. 7 shows, by way of example, the calculation stages within a convolutional layer of a CNN. The input (51) into a convolutional layer (52) of a CNN can be processed in three stages. The three stages can comprise a convolution stage (53), a detector stage (54) and a collection stage (55). The convolutional layer (52) can then output data to a subsequent convolutional layer (56).

Figure 8:
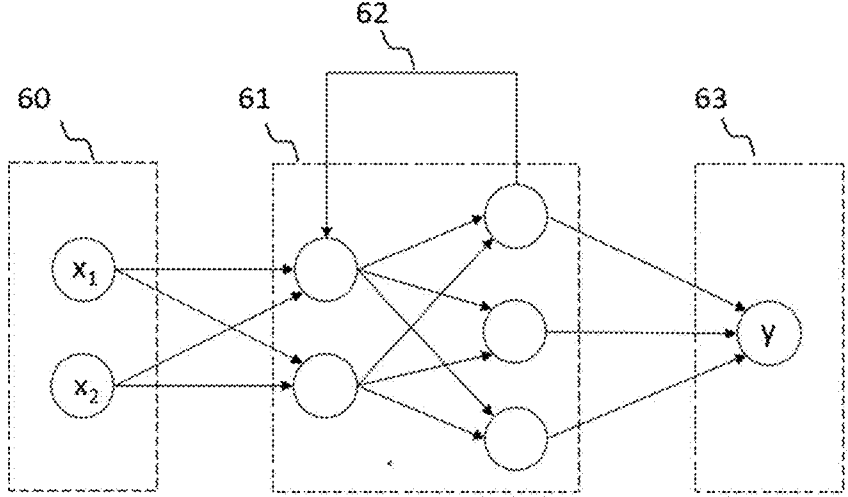

FIG. 8 shows, by way of example, a recurrent neural network. In a recurrent neural network (RNN), the previous state of the network influences the output of the current state of the network. The RNN depicted comprises an input layer (60) that receives an input vector ($x_1$, $x_2$), hidden layers (61) having a feedback mechanism (62), and an output layer (63) to output a result.

Figure 9:
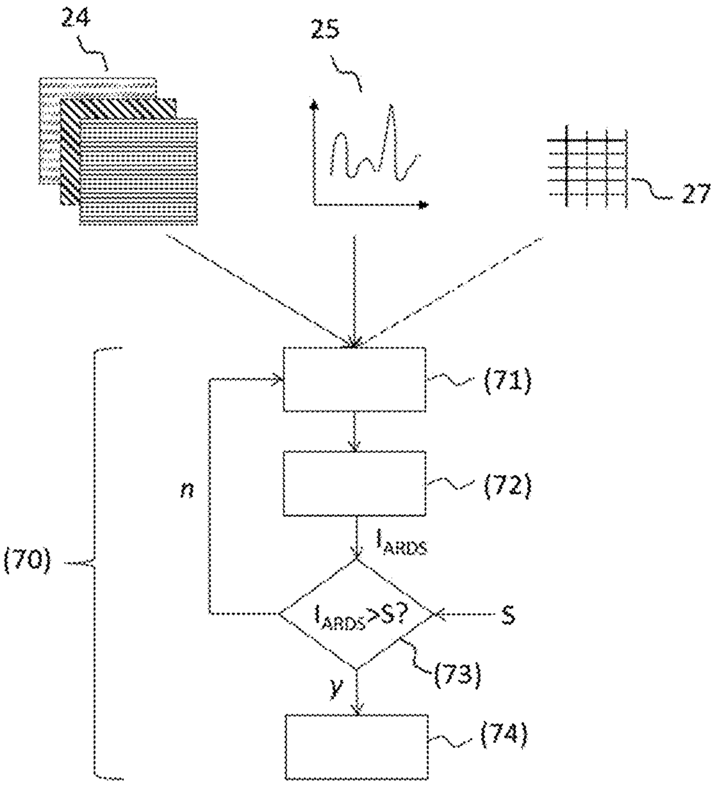

FIG. 9 shows schematically in the form of a flow chart one embodiment of the method (70) according to the disclosure. In a first step (71), patient data are received. The patient data comprise a plurality of radiological images (24) of the thorax of an intensive care patient, a plurality of vital data (25) relating to vital parameters of the intensive care patient, and optionally further data (27).

In a further step (72), the patient data are supplied to an artificial neural network. The artificial neural network is configured to determine an ARDS indicator value on the basis of the patient data. In a further step (73), said ARDS indicator value is compared with a threshold value ("$I_{ARDs}$>S"?). If there is a defined deviation between the ARDS indicator value and the threshold value ("y"), a notification is output in a further step (74), indicating that the probability of ARDS occurring in the intensive care patient is high. On the other hand, if the probability of ARDS being present is low ("n"), no notification is given; instead, the method (70) according to the disclosure is passed through again once new patient data are available.

Figure 10:
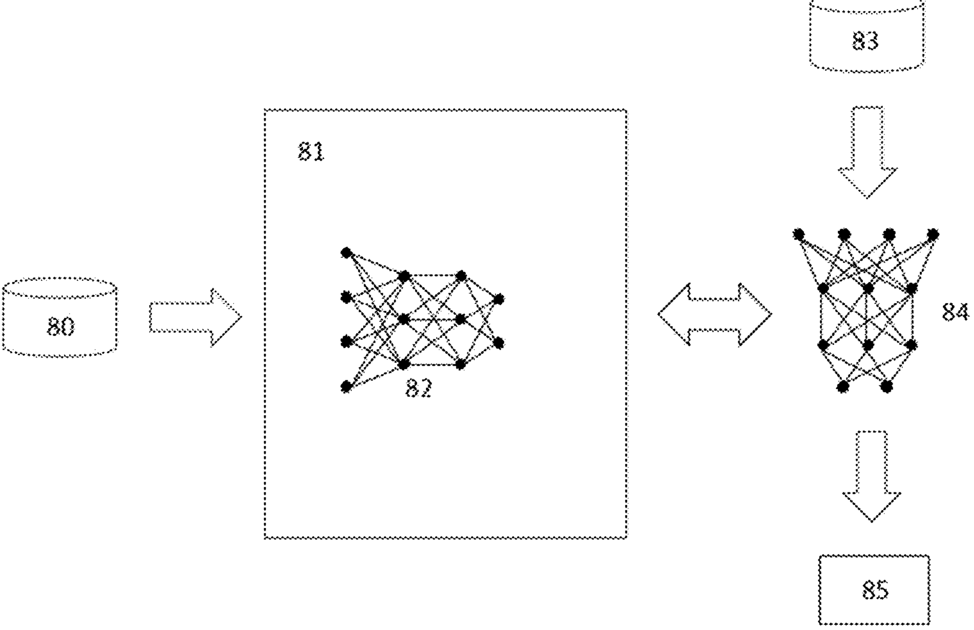

FIG. 10 shows, by way of example, training of an artificial neural network. Once a given network (82) has been structured for a task, the neural network is trained using a training data set (80). To start the training process, the initial weights can be chosen at random or by pretraining, for example using a deep belief network. The training cycle can then be either supervised or run unattended. Supervised learning is a learning method in which the training is performed as a mediated operation, for example when the training data set (80) contains an input paired with the desired output for the input or when the training data set contains an input with a known output. The network processes the inputs and compares the resulting outputs with a set of expected or desired outputs. The weights are then altered in such a way that the error is minimized. The training framework (81) can provide tools for monitoring how well the untrained neural network (82) is converging toward a model suitable for generating correct responses on the basis of known input data. The training process can be continued until the neural network reaches a statistically desired accuracy. The trained neural network (84) can then be used for generating an output for new data.

Figure 11:
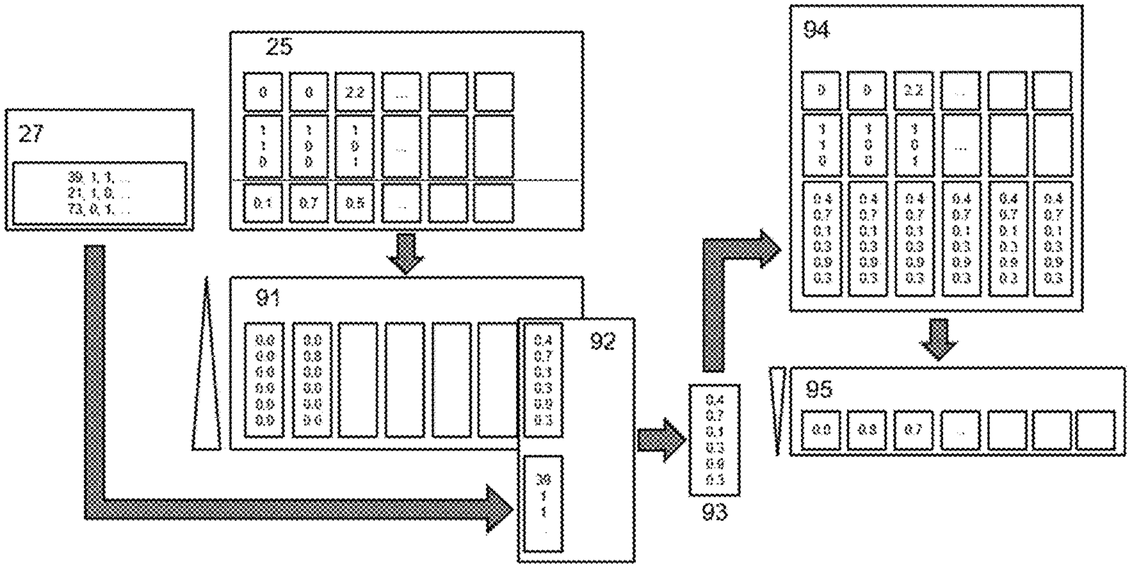

FIG. 11 shows, by way of example and schematically, one possibility of processing of vital data (25) and further data (27) by means of an artificial neural network. The artificial neural network comprises a subnetwork (91) having a plurality of feedback layers for processing of the time information in the vital data (25). The processed vital data are merged with the further data (27) in a subnetwork (92) having a plurality of fully connected layers. The merged data are then supplied to a bottleneck (93) of a defined size in order to achieve a dimensionality reduction. The data are then reconstructed (94). What follows in turn is a subnetwork (95) having a plurality of feedback layers for generating a representation of the original data (25, 27). The structure of the subnetworks (91)→(92)→(93)→(94)→(95) corresponds to an autoencoder.

The invention claimed is:

1. A computer system comprising
an input unit,
a control and calculation unit, and
an output unit,
wherein the control and calculation unit is configured to prompt the input unit to receive patient data relating to an intensive care patient, wherein the patient data comprises at least the following patient data:
a plurality of radiological images of a thorax of the intensive care patient, wherein the plurality of radiological images show the thorax at different times, and
a plurality of vital data relating to vital parameters of the intensive care patient, wherein the vital data specify values relating to the vital parameters at different times,
wherein the control and calculation unit is configured to supply the received patient data to an artificial neural network, wherein the artificial neural network comprises:
a plurality of parallel first subnetworks, each configured to receive a respective one of the plurality of radiological images and generate a time-dependent image descriptor therefor, wherein each of the plurality of parallel first subnetworks has an identical structure and weights;
a second subnetwork configured to receive the plurality of vital data and generate time-dependent vital data descriptors therefor; and
a third subnetwork comprising an output layer and configured to merge the time-dependent image descriptors from the plurality of parallel first subnetworks and the time-dependent vital data descriptors from the second subnetwork,
wherein the merged descriptors are supplied to layers in the third subnetwork that comprise feedback neurons,
wherein the artificial neural network has been trained using reference data to calculate an ARDS indicator value based on the patient data and to output the ARDS indicator value via the output layer,
wherein the control and calculation unit is configured to receive the ARDS indicator value from the artificial neural network,
wherein the control and calculation unit is configured to compare the ARDS indicator value with a threshold value, and
wherein the control and calculation unit is configured to prompt the output unit to output a notification if the ARDS indicator value deviates from the threshold value in a defined manner.

2. The computer system of claim 1, wherein the plurality of radiological images comprise at least three X-rays images of the thorax of the intensive care patient, wherein at least one X-ray image has been generated within an immediately preceding twelve hours period, preferably within an immediately preceding three hours period.

3. The computer system of claim 1, wherein the vital parameters are selected from a group comprising: heart rate, respiratory rate, blood pressure, body temperature, blood oxygen saturation, partial pressure of oxygen, fraction of inspired oxygen, oxygenation index and/or blood pH of the intensive care patient.

4. The computer system of claim 1, wherein the control and calculation unit is configured to prompt the input unit to receive further patient data relating to the intensive care patient, wherein the further patient data are selected from a group comprising: age, sex, body weight, height, existing disease(s) and/or previous disease(s) of the intensive care patient, wherein the control and calculation unit is configured to supply the further patient data to the third input layer.

5. The computer system of claim 1, wherein the notification comprises recommended actions to be taken by a physician or hospital staff to prevent deterioration of a state of health of the intensive care patient.

6. The computer system of claim 1, wherein the computer system is further configured to monitor a state of health of the intensive care patient in an intensive care unit of a hospital based on the vital parameters.

7. The computer system of claim 1, wherein the computer system can access at least one database of a hospital in which some of the patient data are stored.

8. The computer system of claim 1, wherein the computer system is configured to calculate a new ARDS indicator value whenever new defined patient data are available.

9. The computer system of claim 1, wherein the first subnetwork is a CNN or comprises a CNN and/or wherein the third subnetwork is an RNN or comprises an RNN.

10. A method for detecting ARDS in an intensive care patient, comprising:

receiving patient data relating to the intensive care patient, wherein the patient data comprises at least the following patient data:

a plurality of radiological images of a thorax of the intensive care patient, wherein the plurality of the radiological images show the thorax at different times, and a plurality of vital data relating to vital parameters of the intensive care patient, wherein the vital data specify values relating to the vital parameters at different times, supplying the patient data to an artificial neural network, wherein the artificial neural network comprises:

a plurality of parallel first subnetworks, each configured to receive a respective one of the plurality of radiological images and generate a time-dependent image descriptor therefor, wherein each of the plurality of parallel first subnetworks has an identical structure and weights;

a second subnetwork configured to receive the plurality of vital data and generate time-dependent vital data descriptors therefor; and a third subnetwork comprising an output layer and configured to merge the time-dependent image descriptors from the plurality of parallel first subnetworks and the time-dependent vital data descriptors from the second subnetwork, wherein the merged descriptors are supplied to layers in the third subnetwork that comprise feedback neurons, wherein the time-dependent image descriptors and the time-dependent vital data descriptors are supplied to layers in the artificial neural network that comprise feedback neurons, wherein the artificial neural network has been trained using reference data to calculate an ARDS indicator value based on patient data and to output the ARDS indicator value via the output layer, receiving the ARDS indicator value for the supplied patient data from the artificial neural network, comparing the ARDS indicator value with a threshold value, and outputting a notification if the ARDS indicator value deviates from the threshold value in a defined manner.

11. A non-transitory computer program product comprising a computer program which can be loaded into a memory of a computer system, where it prompts the computer system to execute the following:

receiving patient data relating to an intensive care patient, wherein the patient data comprises at least the following patient data:

a plurality of radiological images of a thorax of the intensive care patient, wherein the plurality of radiological images show the thorax at different times, and a plurality of vital data relating to vital parameters of the intensive care patient, wherein the vital data specify values relating to the vital parameters at different times, supplying the patient data to an artificial neural network, wherein the artificial neural network comprises:

a plurality of parallel first subnetworks, each configured to receive a respective one of the plurality of radiological images and generate a time-dependent image descriptor therefor, wherein each of the plurality of parallel first subnetworks has an identical structure and weights;

a second subnetwork configured to receive the plurality of vital data and generate time-dependent vital data descriptors therefor; and a third subnetwork comprising an output layer and configured to merge the time-dependent image descriptors from the plurality of parallel first subnetworks and the time-dependent vital data descriptors from the second subnetwork, wherein the merged descriptors are supplied to layers in the third subnetwork that comprise feedback neurons, wherein the artificial neural network has been trained using reference data to calculate an ARDS indicator value based on the patient data and to output the ARDS indicator value via the output layer, receiving the ARDS indicator value for the supplied patient data from the artificial neural network, comparing the ARDS indicator value with a defined threshold value, and outputting a notification if the ARDS indicator value deviates from the threshold value in a defined manner.

* * * * *